United States Patent [19]

Scharlack et al.

[11] Patent Number: 5,394,047
[45] Date of Patent: Feb. 28, 1995

[54] ULTRASONIC TRANSDUCER CONTROL SYSTEM

[75] Inventors: Ronald S. Scharlack, Brookline; Wayne E. Marshall, Medway, both of Mass.

[73] Assignee: Ciba Corning Diagnostics Corp., Medfield, Mass.

[21] Appl. No.: 16,625

[22] Filed: Feb. 12, 1993

[51] Int. Cl.⁶ .................. H01L 41/08; G03B 27/76
[52] U.S. Cl. ........................... 310/316; 356/36
[58] Field of Search ............... 310/323, 325, 328, 316, 310/317; 128/24 A; 239/102.2; 259/DIG. 44; 318/116; 356/36; 366/116, 127

[56] References Cited

U.S. PATENT DOCUMENTS

| | | | |
|---|---|---|---|
| 3,885,902 | 5/1975 | Fujieda et al. | 431/1 |
| 3,972,614 | 8/1976 | Johansen et al. | 356/36 |
| 4,116,239 | 9/1978 | Ewen | 128/184 |
| 4,271,371 | 6/1981 | Furuichi et al. | 310/316 |
| 4,445,063 | 4/1984 | Smith | 310/316 |
| 4,524,746 | 6/1985 | Hansen | 123/538 |
| 4,587,958 | 5/1986 | Noguchi et al. | 310/316 X |
| 4,626,728 | 12/1986 | Flachenecker et al. | 310/316 |
| 4,687,962 | 8/1987 | Elbert | 310/316 |
| 4,764,021 | 8/1988 | Eppes | 366/127 |
| 4,849,872 | 7/1989 | Gassler | 363/49 |
| 4,945,062 | 7/1990 | Chiang | 436/11 |
| 4,965,532 | 10/1990 | Sakurai | 310/316 X |
| 4,966,131 | 10/1990 | Houghton et al. | 128/24 A |
| 4,967,753 | 11/1990 | Hasse et al. | 128/662.06 |
| 4,973,876 | 11/1990 | Roberts | 310/316 |
| 4,997,769 | 3/1991 | Lundsgaard | 436/66 |
| 5,121,023 | 6/1992 | Abel | 310/316 |
| 5,151,085 | 9/1992 | Sakurai et al. | 310/316 X |
| 5,180,363 | 1/1993 | Idemoto et al. | 310/316 X |

Primary Examiner—Mark O. Budd
Attorney, Agent, or Firm—Nicholas I. Slepchuk, Jr.; Arthur S. Morgenstern; Judith A. Roesler

[57] ABSTRACT

A control system for providing a drive signal to an ultrasonic transducer and for controlling the tip motion of the ultrasonic transducer wherein the transducer tip is disposed in a hemolyzing chamber. The control system includes a sensor for sensing the motion of the transducer tip and a feedback circuit coupled between the sensor and the transducer where the feedback circuit provides a feedback signal to control the motion of the transducer tip.

8 Claims, 4 Drawing Sheets

ULTRASONIC TRANSDUCER CONTROL SYSTEM

FIELD OF THE INVENTION

This invention relates to control systems and more particularly to ultrasonic transducer control systems used in hemolyzing systems.

BACKGROUND OF THE INVENTION

As is known in the art, hemolysis is the liberation of hemoglobin from red blood cells. Hemolysis may be accomplished by ultrasonic disruption techniques. In ultrasonic disruption, the red blood cells are exposed to an ultrasonic signal which disrupts the cell wall and liberates hemoglobin from the red blood cells.

However if the signal level of the ultrasonic signal is too low, an excessive number of red blood cells remain undisrupted. This results in measurement inaccuracies. On the other hand, if the signal level of the ultrasonic signal is too high, an excessive amount of oxygen may be introduced into the sample or gas bubbles may be introduced into the sample which also results in measurement inaccuracies.

In conventional hemolysis systems, at least a portion of an ultrasonic transducer (i.e. the transducer tip) is disposed in a hemolyzing chamber. An excitation signal is applied to a drive port of the transducer causing the transducer tip to vibrate with an amplitude determined by the load. Conventional ultrasonic transducer driver circuits fail to control the transducer tip motion in response to varying loads in the hemolyzing chamber.

One problem with this approach however, is that as a load disposed in the hemolyzing chamber varies, the transducer provides ultrasonic outputs having varying displacement amplitudes. Thus such driver circuits do not perform adequately in those hemolysis applications where an ultrasonic signal having a relatively constant amplitude is required.

In some applications, for example, the transducer is inherently exposed to varying load conditions. In hemolysis applications wherein the hemolyzing chamber which is initially empty and alternately fills and empties as blood samples of varying characteristics flow therethrough, the load provided to the transducer by the empty and full hemolyzing chamber is substantially different.

It would therefore be desirable in such applications to provide a transducer control system which provides the transducer with a predetermined tip amplitude such that the transducer may provide complete hemolysis of a blood sample while minimizing measurement inaccuracies due to variations in the motion of the transducer tip amplitude.

SUMMARY OF THE INVENTION

In accordance with the present invention, an ultrasonic transducer control system includes an oscillator circuit for providing a drive signal, a pair of pulse generator circuits coupled to the oscillator circuit, wherein each of the pulse generator circuits provides, in response to predetermined portions of the oscillator drive signal, first and second pulse signals having predetermined pulse widths. The control system further includes first and second switches, each of the switches having a first terminal coupled to a corresponding one of the pair of pulse generator circuits and each of the switches having a second terminal coupled to a transformer circuit. The control system further includes a voltage feedback circuit, coupled to the transformer circuit, for controlling the drive voltage to the transformer circuit.

With this particular arrangement, an ultrasonic transducer control system may provide a substantially constant drive voltage to a transducer to thus provide the transducer with a substantially constant tip motion which is independent of the size of a load which is coupled to the transducer. The transducer may be provided, for example, as a hemolyzer transducer having a first portion disposed in a region of a hemolyzing chamber. The piezoelectric device may be provided having a predetermined range of mechanical tip motion when excited by a drive signal having predetermined amplitude and frequency characteristics. The control system excites the transducer at its natural parallel resonance to generate an efficient sinusoidal tip movement, and maintains a programmable and constant drive voltage independent of the load disposed in the hemolyzing chamber. The transducer is provided having a transfer function characteristic corresponding to a linear change of tip motion with applied voltage. However, transfer functions between several of such transducers may vary. Thus, each of several transducers may be measured and labeled with a code to indicate its transfer function. The code may represent, for example, a peak to peak tip motion as provided by a predetermined excitation signal. The control system may be programmed from a look-up table to provide a desired excitation voltage for a particular transducer circuit. Thus the control system may be programmed to compensate for the variations in transfer functions between several transducers. The control system may be programmed by actuating particular ones of a plurality of switches coupled to an analog to digital converter. Thus, the driver circuit enables a transducer to provide a predetermined peak-to-peak tip motion for a particular application regardless of the transfer function of the transducer.

BRIEF DESCRIPTION OF THE DRAWINGS

The foregoing features of this invention as well as the invention itself may be more fully understood from the following detailed description of the drawings in which.

DESCRIPTION OF THE PREFERRED EMBODIMENTS

Figure 1:
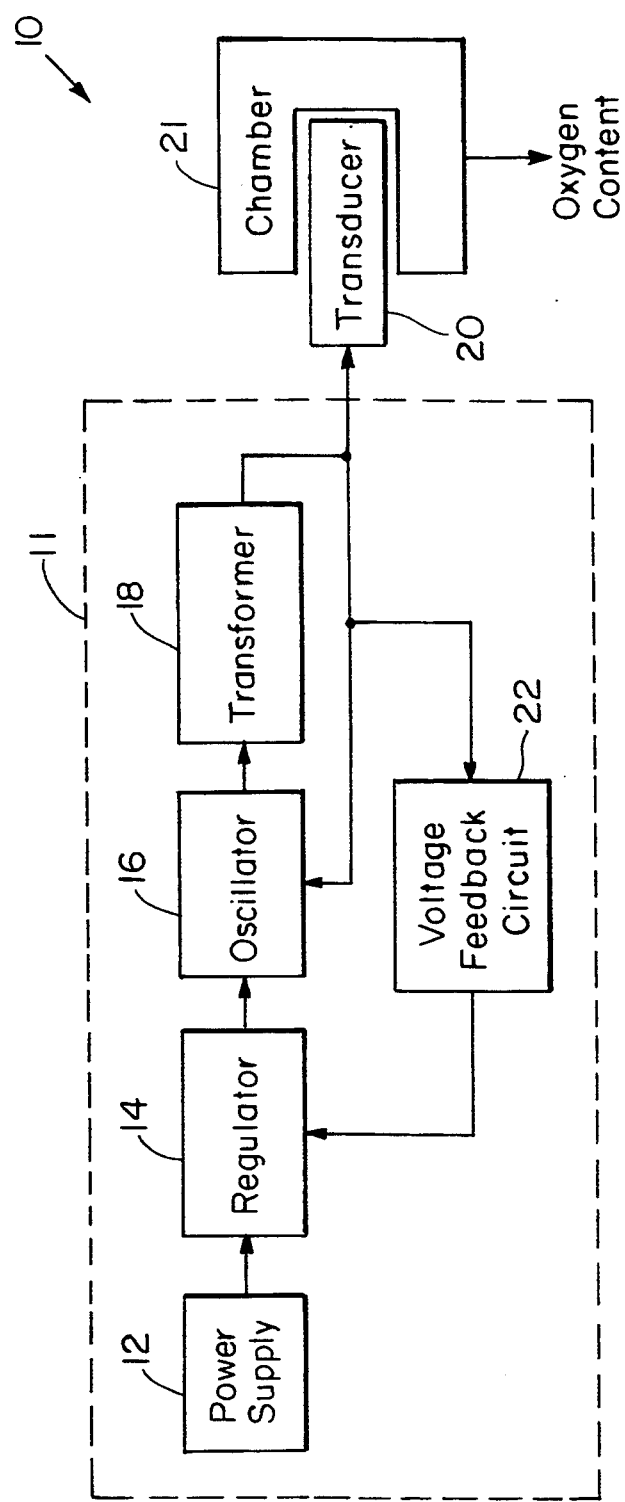
FIG. 1 is a block diagram of a hemolyzing system.

Referring now to FIG. 1, a hemolyzing system 10 includes a control system 11 coupled to an ultrasonic transducer 20 having at least a portion thereof disposed in a hemolyzing chamber 21. The hemolyzing chamber 21 may be alternately filled and emptied with whole blood, for example, and the control system 11 provides a drive signal to the ultrasonic transducer 20. The ultrasonic transducer provides an ultrasonic signal to the chamber 21 to thus separate hemoglobin from red blood cells of the whole blood disposed in the chamber 21.

The control system 11 includes a power supply 12 coupled to a voltage regulator circuit 14. The voltage regulator circuit 14 provides a regulated signal to a first input port 16a of an oscillator 16, here a voltage controlled oscillator circuit 16. In response to the input signal received on the input port 16a, the oscillator circuit 16 provides at output port 16b a signal to a first terminal of a transformer circuit 18.

The transformer 18 couples a first portion the signal fed thereto to an input port of the ultrasonic hemolyzer transducer 20 which may be provided for example as a piezoelectric device. The hemolyzer transducer 20 has at least a portion thereof disposed in the hemolyzing chamber 21. The hemolyzer transducer 20 may be operated for example at a predetermined frequency in a parallel resonance mode. The piezoelectric device may be provided having a predetermined range of mechanical tip motion when excited by a drive signal having predetermined amplitude and frequency characteristics.

A second portion of the transformer output signal is coupled to a second input port of the oscillator circuit 16 to provide a frequency control signal to the oscillator circuit 16. A third portion of the transformer output signal is coupled to an input port of a voltage feedback circuit 22. The voltage feedback circuit 22 couples a portion of the transformer output signal to the regulator circuit 14 to thus provide voltage feedback control of the transformer output signal.

The control system 11 excites the transducer 20 at its natural parallel resonance to generate an efficient sinusoidal tip movement, and maintains a programmable and constant drive voltage independent of the load disposed in the hemolyzing chamber 21.

The transducer 20 is provided having a transfer function characteristic corresponding to a linear change of tip motion with applied voltage. However, transfer functions between several of such transducers may be different. Thus, each of several transducers may be measured and labeled with a code indicative of the transducer transfer function.

The code may represent a peak to peak movement of the transducer tip which results when an excitation signal having a predetermined amplitude and frequency is provided to an input port of the transducer 20. The control system 11 may be programmed to provide a particular drive signal for a particular transducer circuit 20. Thus the control system 11 may compensate for the variations in transfer function of a particular transducer.

Figure 2A:
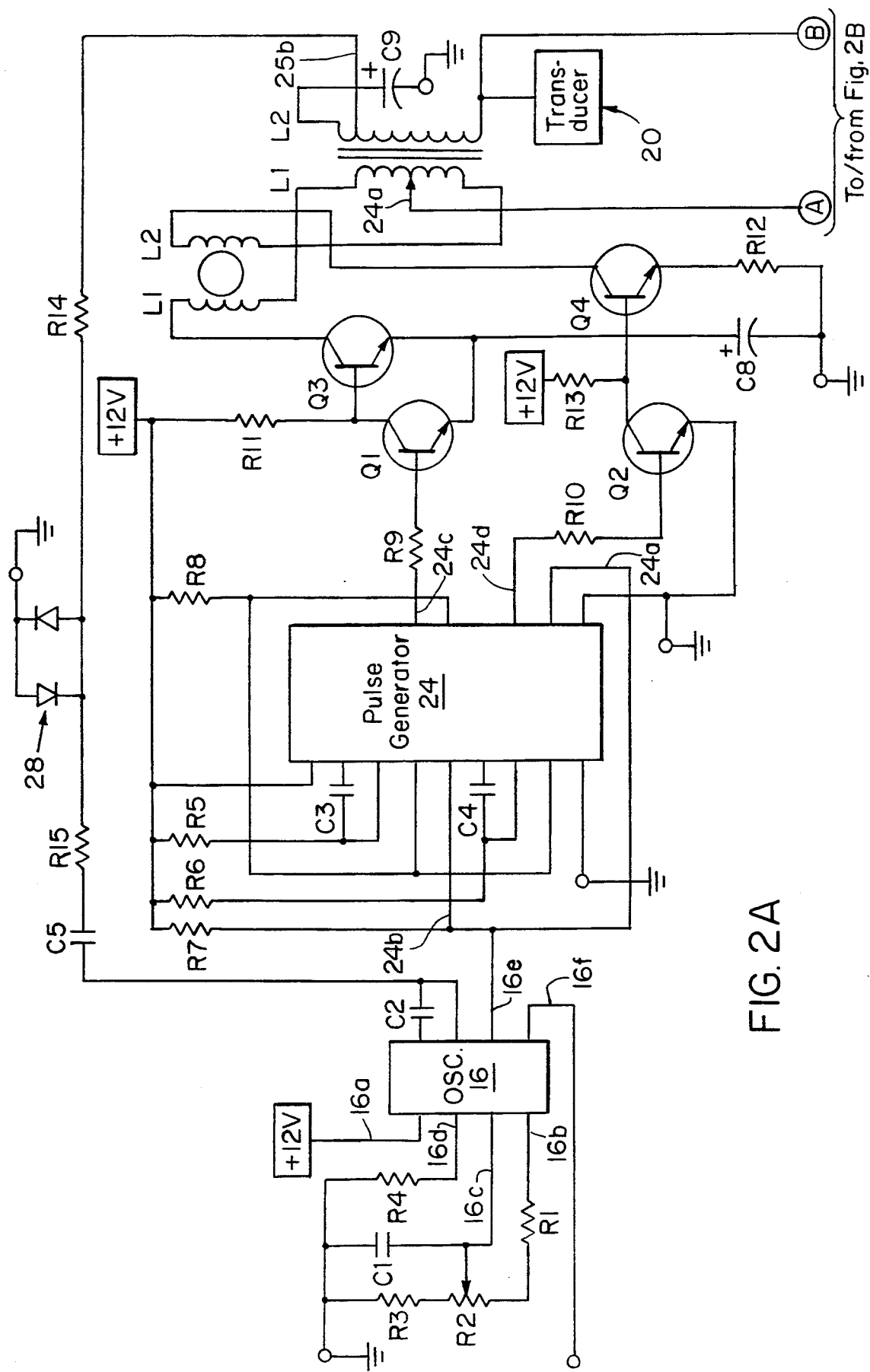
FIGS. 2A–2C is a schematic diagram of a control system for an ultrasonic transducer.
Figure 2B:
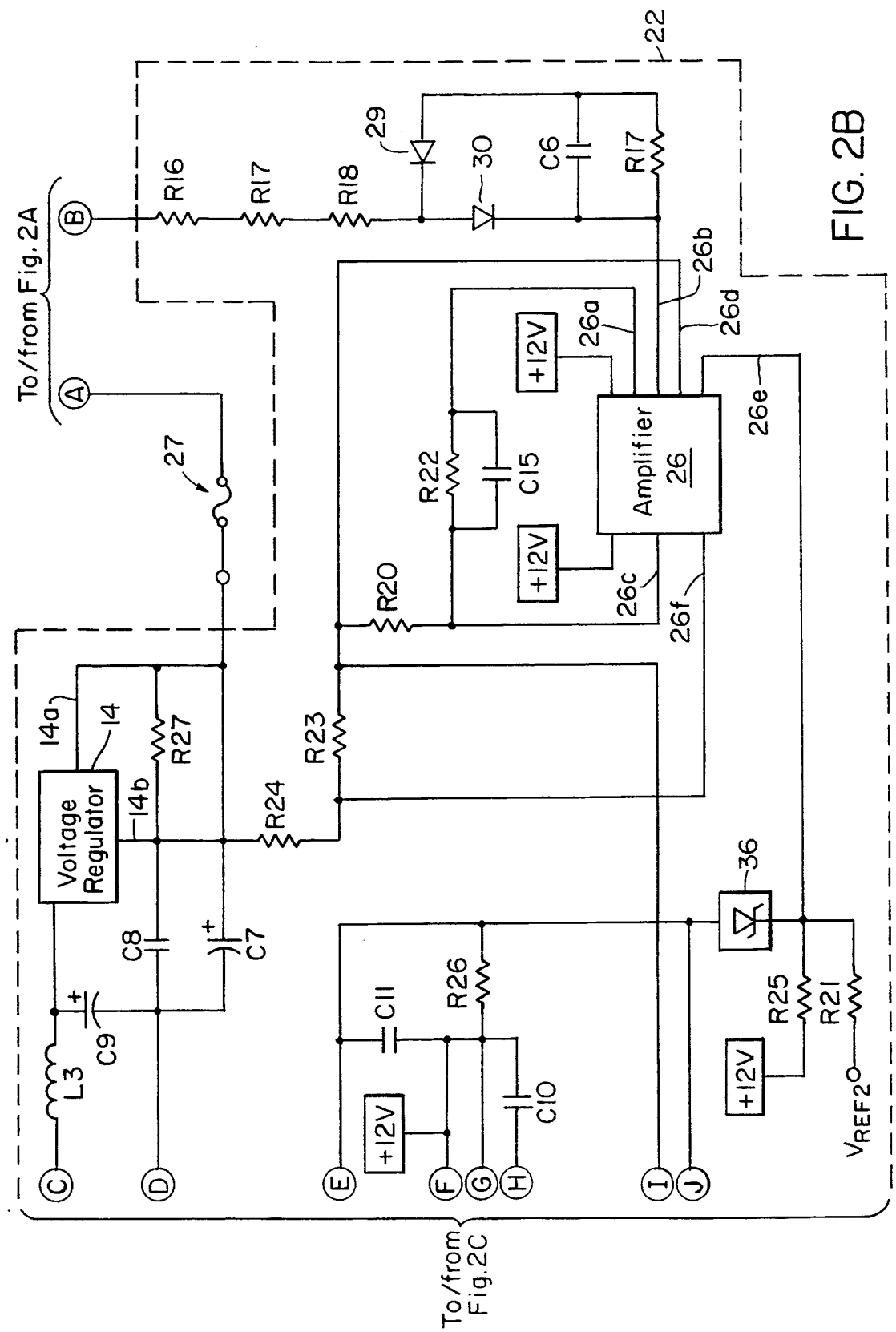
Figure 2C:
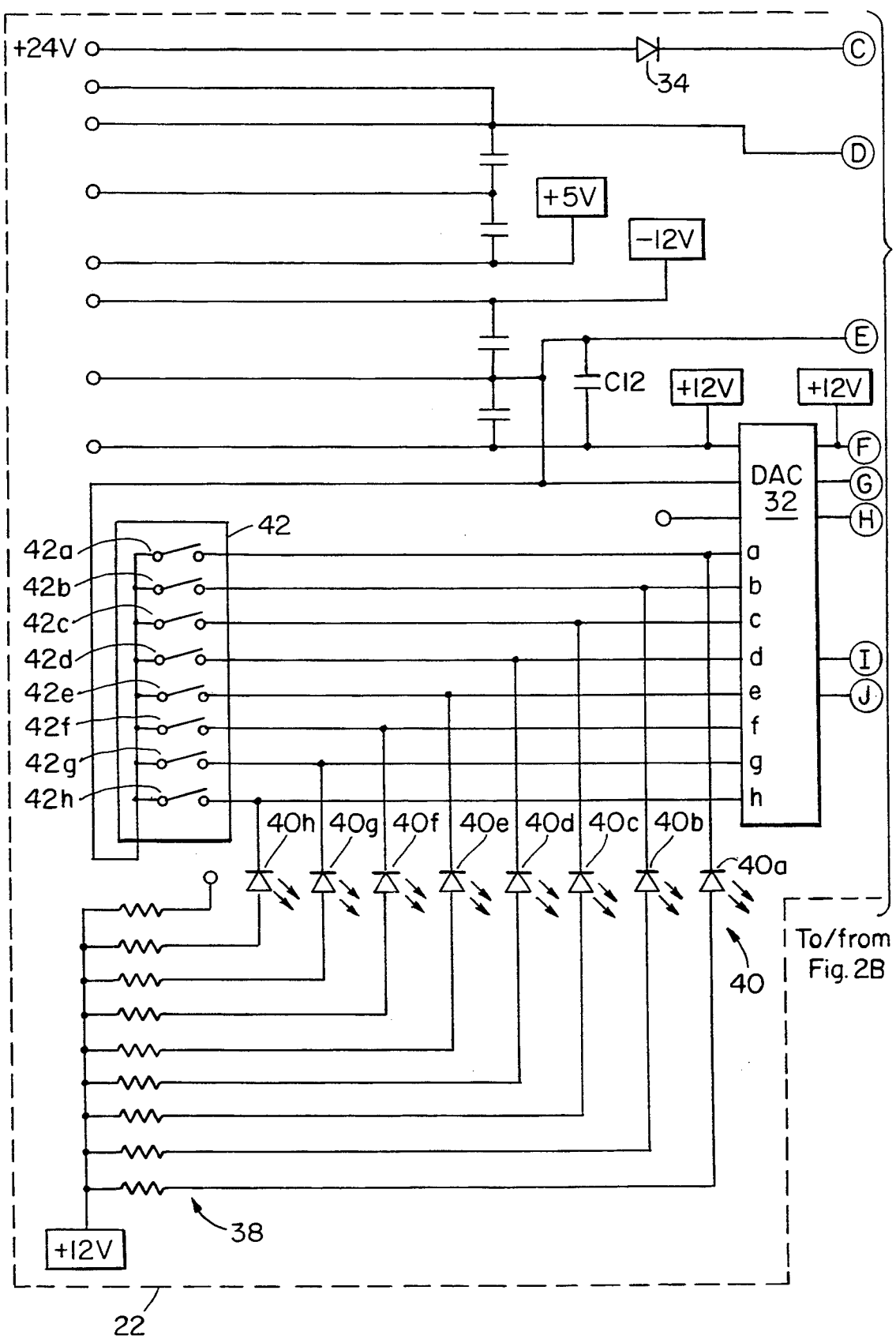

Referring now to FIGS. 2A–2C in which like elements of the hemolyzing apparatus 10 of FIG. 1 are provided having like reference designations, a voltage source V, is coupled to the input port 16a of the voltage controlled oscillator (VCO) 16. The VCO 16 provides a reference voltage at output port 16b and resistors R1, R2 and R3 are coupled as shown to provide an adjustable voltage divider circuit. Filter capacitor C1 filters noise from the voltage divider signal and provides a non-inverting input control voltage signal to an input port 16c of the VCO 16. Resistor R4 terminates at an inverting control voltage input port 16d of the VCO 16. The VCO provides an output signal at output port 16e. The oscillator output signal may be provided for example as a square wave having a frequency typically of about 37 kilohertz (kHz).

A capacitor C2 having one of a range of capacitance values is coupled to the VCO 16. The capacitance value of the capacitor C2 may be varied over a predetermined range to thus provide a corresponding change in the frequency of the VCO output signal. The VCO 16 may be enabled and disabled by application of a logic signal to the VCO control port 16f.

The VCO output signal is fed to a pulse generator circuit 24 which includes a pair of pulse generators. A first one of the pair of pulse generator circuits receives the VCO output signal at an input port 24a and a second one of the pair of pulse generator circuits receives the VCO output signal at an input port 24b. Capacitor C3 and resistor R5 may be provided having values selected to provide a first one of the pair of pulse generator 24 circuit outputs, a first pulse output signal, having a predetermined pulse width at port 24c. The pulse width may be selected, for example, to correspond to about a quarter of the oscillator period. The first pulse output signal is fed to a first terminal of a first transistor Q1, here provided as a bipolar junction transistor (BJT) having base, emitter and collector electrodes connected as shown.

Similarly capacitor C4 and resistor R6 may be selected to provide a second one of the pair of pulse generators 24 having a second pulse output signal having a second predetermined pulse width at port 24d. The second pulse output signal is fed to a first terminal of a second transistor Q2 here provided as a bipolar junction transistor (BJT) having base, emitter and collector electrodes.

Here transistors Q1 and Q2 are provided as BJTs. Those of ordinary skill in the art will recognize of course that transistors Q1, and Q2 (and likewise transistors Q3 and Q4 to be described below) may alternatively be provided as field effect transistors (FETs).

Resistor R7 is coupled between the VCO output port 16c and a reference potential. The resistor R7 acts as a so-called "pull up" resistor for the VCO square wave output signal at the output port 16c. The first pulse generator which feeds a signal to the transistor Q1 may be activated on the positive edge of the VCO square wave output signal while the second pulse generator which feeds a signal to the transistor Q2 may be activated on the negative going edge of the VCO square wave output signal. Resistor R8 is coupled between a reference potential $V_{REF}$ and a plurality of unused input ports to thus enable the pulse generator circuit 24.

Resistors R9 and R10 are coupled as shown between the pulse generator circuit 24 and the transistors Q1, Q2 respectively, to limit the base current to switching transistors Q1 and Q2. When the pulse signal provided from pulse generator 24 at output port 24c is provided having a first logic level, current flows in the base of the switching transistor Q1 and causes the transistor Q1 to saturate through a pull up resistor R11. When the pulse signal at output port 24c is provided having a second different logic level the current through resistor R11 provides a base current to a switching Darlington transistor Q3. Transistors Q2 and Q4 are similarly biased by the output signal from pulse generator output port 24d and resistors R10, and R13. Resistor R12 provides a signal path to ground to the emitter electrodes of transistors Q3 and Q4. Thus resistors R12 limits the average emitter current of transistors Q3 and Q4 as averaged by capacitor C8.

Inductors L1, L2 maintain symmetry in the drive signal provided to each side of a center tapped primary transformer circuit 25. The Center tap of the transformer circuit 25 is coupled to a voltage regulator 14 at a port 14a through a fuse 27.

The secondary side of transformer circuit 25 provides an output signal to drive the transducer 20 through capacitor C9. The transducer 20 may be provided for example as a piezoelectric device which may be driven to operate in a parallel resonant mode. Since the piezoelectric device may operate in the parallel resonant mode, the secondary side of the transformer 25 and the piezoelectric device coupled to provide a resonant tank circuit with a high voltage sinusoid.

A terminal 25b on the secondary side of the transformer 25 provides a low voltage feedback tap. The feedback signal is coupled through resistor R14 and is limited by antiparallel connected diode pair 28. Resistor R15 and capacitor C5 couple the feedback signal to the VCO 16 through capacitor C2. The VCO 16 includes an internal phase lock circuit. The feedback signal provides feedback for adjustment of the frequency and phase to a point where the phase shift through the VCO phase lock circuit is substantially zero. The initial frequency of the VCO 16 is selected to cause the oscillator loop to lock on the parallel resonant point instead of the series resonant point of transducer 20.

The voltage feedback circuit 22 couples a portion of the output signal from the secondary side of the transformer 25 and provides a control signal to the primary side of the transformer 25 to establish a constant transducer tip motion.

Resistors R16, R17, R18 and R19 are coupled to the output terminal of the transformer 25 secondary as shown to provide a voltage divider circuit. Diodes 29 and 30 and capacitor C6 are coupled to the voltage divider circuit as shown to thus provide a feedback signal from an attenuated average sample of the drive voltage signal provided to the transducer 20.

Amplifier circuit 26 here includes a pair of amplifiers. Terminals 26a and 26b provide input ports for a non-inverting unity gain buffer amplifier having an output port 26c. Resistor R22 and capacitor C15 provide a stabilizing feedback circuit for the buffer amplifier. The buffered signal is fed through resistor R20 to a high gain difference amplifier at input terminal 26d. Terminal 26e is coupled to a reference potential $V_{REF2}$. Difference amplifier output terminal 26f provides an output signal to the voltage regulator 14 through resistor R24.

A digital to analog converter (DAC) 32 provides a bias current through the resistor R20. The bias current offsets the signal from buffer amplifier output port 26c relative to the difference amplifier output at the output port 26f which is held at a first predetermined DC reference voltage by a reference diode 36. The difference current between DAC 32 and the current supplied by difference amplifier 26 through the resistor R20 when the output signal at output port 26f correspond to the first reference value should flow through feedback resistor R23. Thus the amplifier error signal at amplifier output port 26f corresponds to the reference value −/+ the error current times the resistance value of the reversed biased diode which corresponds to a value typically of about 1 megohm.

This error signal is coupled to a first electrode of the resistor R24 which is also the termination of a voltage divider circuit provided by resistors R27 and R24. The voltage across the resistor R27 is set by the voltage regulator 14 which forces the voltage across R24 to be in a ratio to the resistance values of the resistors R24 and R27.

Capacitor C7 filters the output of voltage regulator 14 while capacitor C8 filters the control voltage of the voltage regulator 14. Inductor L3 and capacitor C9 filter the input voltage to the regulator 14 while diode 34 prevents damage to the circuit which may occur due to reverse polarity of a +24 volt DC power supply. The voltage control loop is thus closed with one inversion at amplifier 26 such that if the piezoelectric drive voltage is too small the drive voltage to the control terminal 14a of voltage regulator 14 will become more positive which will supply a larger voltage to the switching transistors Q3 and Q4 on the primary of transformer 25 and increase the piezoelectric drive voltage.

The current that establishes the set point for the piezoelectric drive voltage is provided by the digital to analog converter 32. Resistor R25 provides current to reference diode 36 which then biases the reference to digital to analog converter 32 at a predetermined reference voltage through bias compensation resistor R21. This results in a reference current being provided through matching resistor R26 which sets the full scale current of digital to analog converter 32. Capacitor C10 compensates an internal amplifier of the DAC 32 and prevents the amplifier from providing an oscillation signal at the output port thereof. Capacitors C11 and C12 filter the power supply signals fed to the digital to analog converter 32.

Resistor network 38 pulls up each of the DAC logic inputs 32a–32h through light emitting diodes (LEDs) 40a–40h generally denoted 40 and sets all inputs high when switches 42a–42h in switch bank 42 are open. Selectively closing predetermined ones of the switches 42a–42h sets the binary control word in the DAC 32 to control the output current. Thus if the DAC 32 is provided as an 8 bit DAC then the output current may be controlled in 255 distinct steps ranging from no current to full scale current. Thus the control range for the piezoelectric drive voltage may be divided into a plurality of selectable set points.

When a particular one of the switches 42a–42h switch in switch bank 42 is closed, the current drawn through the corresponding LED 40a–40h causes the LED to emit light. Thus here, the LED's 40 provide a visual indication of the state of the DAC control word. Those of ordinary skill in the art will recognize that any conventional indication means may also be used.

In operation, the oscillator circuit 16 provides a symmetric square wave drive signal to each of the pair of one-shot pulse generators in pulse generator circuit 24. The square wave signal is provided having a predetermined frequency. Each pulse generator provides in response to the drive signal a pulse having a predetermined pulse width. For example, the first pulse generator may provide a first pulse at the rising edge of the square wave signal, and the second pulse generator may provide a second pulse at the falling edge of the square wave signal. The pulses may be used to drive the grounding switches Q1–Q4 coupled as shown to opposing primary terminals of the center tapped step-up transformer 25. The center tap 25a is coupled to an output port 14a of the voltage regulator circuit 14 such that the primary switching amplitude is controlled by the voltage regulator 14.

The secondary of the step-up transformer 25 may be coupled to the transducer circuit 20 which may be provided as a piezoelectric device. The transformer 25 may drive the piezoelectric device in a parallel resonant mode with a sinusoidal, high voltage signal. To provide the parallel resonant frequency, a small signal tap 25b on the secondary senses the voltage phase and provides a feedback signal to the oscillator 16. As the transducer drive signal changes in frequency from below parallel resonance to above parallel resonance, the phase shifts rapidly from plus 90 degrees to minus 90 degrees. The oscillator 16 tends to oscillate at the frequency that results in about 0 degrees for that particular transducer thus, setting the oscillation at the parallel resonance frequency. At parallel resonance, the current and power load will be at a minimum.

To maintain a constant voltage drive to the transducer 20, the regulator circuit 14 controls the drive voltage to the step-up transformer 25. The voltage feedback circuit 22 including the voltage divider circuit provided from resistors R16–R19, rectifier circuit provided from diodes 29 and 30 and filter capacitor C6 monitors the drive signal by coupling a portion of the signal though the voltage divider circuit, rectifying and filtering the signal, and amplifying the signal before comparing the signal with a programmable reference level set by the DAC 32 to provide a difference signal. The difference signal is inverted and amplified in amplifier 26, and coupled to the regulator circuit 14 to provide a voltage feedback signal to the regulator circuit 14. The gain of the amplifier stage reduces the output impedance of the step-up transformer 25 and holds the excitation voltage constant with changing transducer load current.

Each of the plurality of switches 42 may be selectably switched to provide a corresponding bit of the DAC 32 having a particular logic value. The selection of bits in the DAC 32 determines the transducer excitation value. The like plurality of LEDs 40 are coupled to corresponding ones of the switches 42 and emit a light to provide an indication of proper switch operation and the value of the DAC word. Thus a particular excitation value may be provided to a transducer having particular predetermined transducer characteristics.

Having described preferred embodiments of the invention, it will now become apparent to one of ordinary skill in the art that other embodiments incorporating the concepts may be used. It is felt, therefore, that these embodiments should not be limited to disclosed embodiments but rather should be limited only by the spirit and scope of the appended claims.

What is claimed is:

1. A hemolyzer transducer control system, for providing a drive voltage to a transformer primary winding wherein the transformer secondary winding is coupled to an ultrasonic transducer having a transducer tip disposed in a hemolyzing chamber, said control system comprising:
   a signal source for providing a drive signal;
   a switch circuit, coupled to said signal source for alternately coupling first and second terminals of the transformer primary winding to a first reference potential in response to the drive signal;
   a voltage regulator circuit having a first port coupled to the transformer primary winding; and
   a feedback circuit, having a first terminal coupled between the transformer secondary winding and said voltage regulator circuit, for providing a control signal to provide the transducer tip having a predetermined tip motion amplitude.

2. The hemolyzer transducer control system of claim 1 further comprising means, coupled to said feedback circuit for providing a programmable reference signal having a predetermined signal level and for providing a difference signal to said voltage regulator circuit wherein the difference signal corresponds to the difference between the signal level of the reference signal and the control signal.

3. A hemolyzing system comprising:
   a hemolyzing chamber;
   an ultrasonic transducer having at least a portion thereof disposed in the hemolyzing chamber and having an input port adapted to receive a drive voltage and having a tip motionally excited by the drive voltage wherein the motion of the tip corresponds to the magnitude of the drive voltage over a predetermined voltage range;
   a control circuit, coupled to said transducer, for providing an output voltage representative of an applied frequency and an applied voltage level, said output voltage applied to the input port of said ultrasonic transducer, said control circuit including:
   a pair of switching transistors powered by said applied voltage level and driven by said pulses to provide said output voltage to said transducer;
   a transformer coupled to said switching transistors on a primary winding and to said transducer on an output winding;
   a sensor, coupled to said transducer, for sensing the motion of the transducer tip and for providing a voltage control signal to said control circuit wherein the voltage control signal is provided having a magnitude to maintain the motion of said tip at a predetermined amplitude;
   a coupling from said transformer output winding to said sensor;
   a pulse generator for providing pulses at said predetermined frequency;
   a solid state switching circuit responsive To said pulses and switching said applied voltage level to provide said output voltage to said transducer; and
   a voltage regulator, for providing said applied voltage level in response to the control voltage provided from said sensor.

4. The system of claim 3 further including:
   an amplifier for the sensed motion and operating to control the voltage regulator in generating the applied voltage level.

5. The system of claim 3 further including:
   a biasing circuit adjusting the voltage regulator according to one of plural selectable biases to cause the applied voltage level to assume one of plural selectable levels.

6. The system of claim 5 further including:
   a digital setting selector; and
   a converter establishing an analog level of bias for said biasing circuit from said digital setting selector.

7. The system of claim 3 further including:
   a center tap on the input winding of the transformer to which said applied voltage level is coupled.

8. The system of claim 3 further including:
   a bipolar circuit for the generated pulses causing pulses representative of opposite drive polarities to be generated and coupled to respective ones of said pair of switching transistors.

* * * * *